Sept. 14, 1976 J. H. ENNS Plant Pat. 3,952
NECTARINE TREE
Filed Nov. 20, 1975
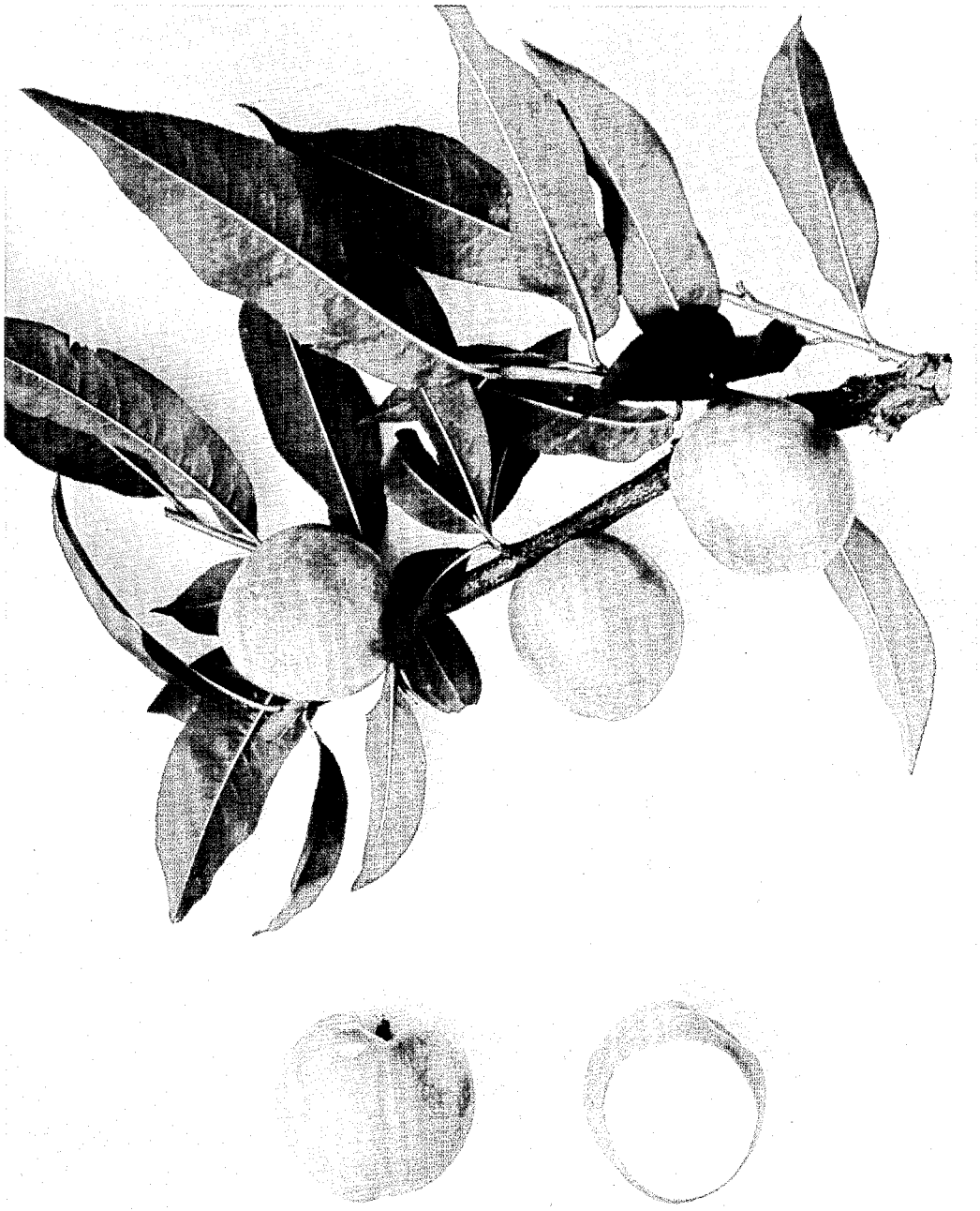

United States Patent

Plant Pat. 3,952

Patented Sept. 14, 1976

3,952

NECTARINE TREE

John H. Enns, 39572 Road 64, Dinuba, Calif. 93618

Filed Nov. 20, 1975, Ser. No. 633,946

Int. Cl.[2] A01H 5/03

U.S. Cl. Plt.—41 1 Claim

ABSTRACT OF THE DISCLOSURE

A nectarine tree which is of medium to large size, vigorous, of open vase form, spreading, stocky of trunk and branches, foliated with lanceolate leaves having a finely serrated margin, and bearing medium size, early ripening, semi-clingstone fruit having yellow skin substantially overspread with red, and yellow flesh.

ORIGIN OF THE VARIETY

The present variety of nectarine tree was discovered by me growing—apparently as a full tree mutation—in an orchard of Mayred (U.S. Plant Pat. No. 2,758) nectarine trees on my ranch located near Dinuba, Tulare County, Calif.; the discovery having been made by me on the occasion of my recognition that the original tree of the present variety had certain distinctive fruit characteristics in comparison to adjacent Mayred trees. I, therefore, continued to observe the original tree to further confirm its novelty and in contemplation of asexual reproduction preparatory to commercial growing thereof.

ASEXUAL REPRODUCTION OF THE VARIETY

Subsequent to my discovery of the present variety of nectarine tree, such variety was successfully asexually reproduced, on my behalf, by a commercial nursery; the reproduction having been accomplished by budding on peach rootstock. The trees, as thus reproduced, ran true to the original tree in all respects. The variety is readily successfully reproduced by budding and grafting.

SUMMARY OF THE VARIETY

The present variety of nectarine tree is generally characterized by a tree which is of medium to large size, vigorous, of open vase form, spreading, stocky of trunk and branches, foliated with lanceolate leaves having a finely serrated margin, and bearing medium size, early ripening, semi-clingstone fruit having yellow skin substantially overspread with red, and yellow flesh.

The present variety of nectarine tree is further, and more particularly, characterized, in comparison to the Mayred, by larger average fruit size and by ripening about three days earlier. Additionally, and exceptional in an early ripening nectarine, the fruit evidences no defects such as soft sutures, split pits, nor abnormal fruit drop.

BRIEF DESCRIPTION OF THE DRAWING

The drawing is an illustration, by photographic reproduction in color, of a twig with leaves and fruit, and separate fruit—one of which is partially cut away to expose the flesh.

DESCRIPTION OF THE VARIETY

The botanical details of this new and distinct variety of nectarine tree—with color definitions (except those in common color terms) referenced to Maerz and Paul Dictionary of Color—are as follows:

Tree:
- *Size.*—Medium to large.
- *Vigor.*—Vigorous.
- *Growth.*—Spreading.
- *Form.*—Open vase.
- *Hardiness.*—Adapted to moderate climate.

- *Production.*—Fruitful.
- *Bearing.*—Regular.

Trunk:
- *Size.*—Stocky.
- *Growth.*—Well developed. Sturdy.
- *Texture.*—Coarse.
- *Color.*—Brown—dark grey.

Branches:
- *Size.*—Stocky.
- *Growth.*—Well developed. Sturdy.
- *Texture.*—Coarse.
- *Color.*—Brown—dark grey.
- *Lenticels.—Number.*—Few. *Size.*—Small.

Leaves:
- *Size.*—Medium to large. Length — 5½" — 7". Width—1½"—1¾".
- *Form.*—Lanceolate.
- *Texture.*—Top surface—glossy. Pubescence absent on under surface.
- *Margin.*—Finely serrated.
- *Petiole.*—Medium size. Average length—½".
- *Glands.*—Reniform. Small to medium. Opposite. Pale yellow.
- *Stipules.*—Wanting.
- *Color.*—Top side—Medium green (23–L–9). Under side—Lighter green (22–K–6).

Flower buds:
- *Hardiness.*—Hardy for California nectarine-producing areas.
- *Dormency requirement.*—Estimated at 550 hours chilling below 45° F.
- *Form.*—Plump. Uniform, slightly pointed at tip.
- *Growth.*—Well developed.

Flowers:
- *Blooming period.—Date of first bloom.*—February 26, 1974. March 1, 1975.
- *Type.*—Generally same as Maygrand.

Fruit:
- *Maturity when described.*—Firm ripe.
- *Date of first picking.*—May 16, 1974. May 19, 1975.
- *Date of last picking.*—May 24, 1974. May 26, 1975.
- *Size.*—Medium. Average diameter axially—2¼". Average transversely in suture plane—2".
- *Form.*—Globose. Uniform. Well rounded at apex.
- *Suture.*—Smooth. Well filled. No marked depression. Very firm over entire suture line.
- *Ventral surface.*—Uniformly rounded.
- *Cavity.*—Uniformly flared. Shallow.
- *Base.*—Very uniform. Broad. Rounded.
- *Apex.*—Uniformly rounded, without point. Slightly depressed.
- *Pistil point.*—Wanting.

Skin:
- *Texture.*—Smooth. Glossy.
- *Color.*—Yellow (12–L–3) substantially overspread with red (6–L–6) with some mottling and streaking.

Flesh:
- *Amygdalin.*—Wanting.
- *Juice.*—Moderate.
- *Texture.*—Medium to firm.
- *Fibers.*—Extend from the pit cavity.
- *Ripens.*—Evenly.
- *Flavor.*—Subacid. Distinct.
- *Aroma.*—Pronounced.
- *Eating quality.*—Good
- *Color.*—Yellow (10–L–5).

Stone:
- *Type.*—Semi-clingstone. Frees from flesh only when soft ripe.
- *Size.*—Medium. Average length—1⅜". Average breadth—1". Average thickness—¾".

*Form.*—Oblong. Sharply pointed at pistil.
*Hilum.*—Oblong. Narrow. Indented.
*Apex.*—Acuminate. Abruptly pointed.
*Sides.*—Non-uniform.
*Surface.*—Irregularly furrowed. Deeply pitted.
*Ridges.*—Sharp. Interrupted. On both sides.
*Ventral edge.*—Coarsely serrated. Becomes small near apex.
*Dorsal edge.*—Pronounced. Finely ridged. Non-uniform near apex.
*Color.*—Tan (11–J–4).
*Tendency to split.*—None.
*Pit.*—Light amber at soft ripe maturity of fruit.
*Fertility.*—Self-fertile.

Use: Dessert.

Keeping quality: Packed at firm ripe maturity, fruit retains exceptional firmness during normal transport to commercial markets.

Resistance to diseases: Equal to other commercial nectarine varieties.

The tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is of medium to large size, vigorous, of open vase form, spreading, stocky of trunk and branches, foliated with lanceolate leaves having a finely serrated margin, and bearing medium size, early ripening, semi-clingstone fruit having yellow skin substantially overspread with red, and yellow flesh; the variety being particularly characterized, in comparison to the Mayred, by larger average fruit size and by ripening about three days earlier.

No references cited.

ROBERT E. BAGWILL, Primary Examiner